(12) United States Patent
Netsch et al.

(10) Patent No.: US 12,236,501 B2
(45) Date of Patent: Feb. 25, 2025

(54) LATENCY COMPENSATION FOR IMAGE PROCESSING DEVICES

(71) Applicant: KONINKLIJKE PHILIPS N.V., Eindhoven (NL)

(72) Inventors: Thomas Netsch, Hamburg (DE); Frank Michael Weber, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 65 days.

(21) Appl. No.: 17/800,328

(22) PCT Filed: Feb. 16, 2021

(86) PCT No.: PCT/EP2021/053714
§ 371 (c)(1),
(2) Date: Aug. 17, 2022

(87) PCT Pub. No.: WO2021/165228
PCT Pub. Date: Aug. 26, 2021

(65) Prior Publication Data
US 2023/0069292 A1    Mar. 2, 2023

(30) Foreign Application Priority Data
Feb. 17, 2020    (EP) .................................... 20157687

(51) Int. Cl.
*G06T 15/00*    (2011.01)
*A61B 6/46*    (2024.01)
(Continued)

(52) U.S. Cl.
CPC .............. *G06T 11/00* (2013.01); *A61B 6/463* (2013.01); *G06T 1/20* (2013.01); *G06V 10/761* (2022.01);
(Continued)

(58) Field of Classification Search
CPC ......... G06T 11/60; G06T 1/20; G06T 19/006; G06T 11/00; G06T 7/254; G06T 2210/41;
(Continued)

(56) References Cited

U.S. PATENT DOCUMENTS 6,496,716 B1    12/2002    Langer
9,990,723 B2 *    6/2018    Van Leeuwen ....... G06T 7/0014
(Continued)

FOREIGN PATENT DOCUMENTS

CN    106156434 A    11/2016

OTHER PUBLICATIONS

Niazi MK, Parwani AV, Gurcan MN. Digital pathology and artificial intelligence. The Lancet. Oncology. May 1, 2019;20(5):e253-61.*
(Continued)

*Primary Examiner* — Phu K Nguyen (57) ABSTRACT

The present invention relates to latency compensation for image processing devices. In order to assign overlay data to frames of a raw image stream (210), past frames within a selection of frames of the raw image stream are considered, which past frames already underwent image processing. A current frame of the raw image stream (210) is compared to the past frames contained in the selection of frames, and that one of the past frames is identified that is most similar to the current frame. Overlay data from the identified past frame are chosen and assigned to the current frame. Thus, the current frame can be presented together with the assigned overlay data chosen from the most similar past frame and without the need to wait for the result of a computationally expensive and time-consuming image processing of the current frame.

20 Claims, 3 Drawing Sheets

(51) Int. Cl.
*G06T 1/20* (2006.01)
*G06T 11/00* (2006.01)
*G06V 10/74* (2022.01)

(52) U.S. Cl.
CPC ...... *G06T 2210/41* (2013.01); *G06T 2210/52* (2013.01)

(58) Field of Classification Search
CPC ....... G06T 2207/30004; G06T 2210/52; G06T 2207/10016; A61B 6/463; G06V 10/761
USPC ......................................................... 345/418
See application file for complete search history.

(56) References Cited

U.S. PATENT DOCUMENTS

| | | | | |
|---|---|---|---|---|
| 11,628,011 | B2* | 4/2023 | Hodges | G16H 30/40 |
| | | | | 705/2 |
| 11,806,085 | B2* | 11/2023 | Meglan | A61B 34/20 |
| 2007/0237370 | A1 | 10/2007 | Zhou | |
| 2013/0268547 | A1* | 10/2013 | Boroczky | G16H 50/70 |
| | | | | 707/758 |
| 2014/0018677 | A1* | 1/2014 | Sharonov | A61B 18/1477 |
| | | | | 606/42 |
| 2014/0148816 | A1* | 5/2014 | McDonald et al. | A61B 34/10 |
| | | | | 606/130 |
| 2016/0354155 | A1 | 12/2016 | Hodges | |
| 2016/0357443 | A1 | 12/2016 | Li | |
| 2018/0183646 | A1 | 6/2018 | Pfletschinger | |
| 2019/0122330 | A1 | 4/2019 | Saget | |
| 2020/0383730 | A1* | 12/2020 | Hodges | A61B 5/7246 |

OTHER PUBLICATIONS

International Search Report and Written Opinion of PCT/EP2021/053714, dated Mar. 30, 2021.
Rolland, Jannick P. et al "Optical Versus Video See-Through Head-Mounted Displays in Medical Visualization", Presence; Teleoperators and Virtual Environments, vol. 66, No. 4, Jun. 2000, pp. 167-309.
Rogolj, Peter et al "Distance Deviation Measure of Contouring Variability", Radiology and Oncolory, vol. 47, No. 1, 2013, pp. 86-96.
https:/itk.org/Doxygen/html/ImageSimilarityMetricsPage.html, 2022.

* cited by examiner

LATENCY COMPENSATION FOR IMAGE PROCESSING DEVICES

CROSS-REFERENCE TO PRIOR APPLICATIONS

This application is the U.S. National Phase application under 35 U.S.C. § 371 of International Application No. PCT/EP2021/053714, filed on Feb. 16, 2021, which claims the benefit of European Patent Application No. 20157687.3, filed on Feb. 17, 2020. These applications are hereby incorporated by reference herein.

FIELD OF THE INVENTION

The present invention relates to image processing, in particular to an image processing device, to a medical imaging arrangement for processing images, and to a method for processing images. More particularly, the present invention relates to image processing of images that are presented to a user together with overlay data that are determined by an image processing algorithm.

BACKGROUND OF THE INVENTION

For several uses and applications, image frames of a raw image stream are processed to obtain overlay data that are assigned to the frames of the raw image stream, while the overlay data are presented to an operator or a user together with the frames of the raw image stream. Such an approach may generally be referred to as augmented imaging.

For example, in the field of medical imaging devices, interventional guidance applications may be used to show the position of a device like a catheter tip or stent with respect to the body of a person. In such applications, information about the device may be generated by an image processing algorithm and presented to an operator/user together with the raw image stream obtained from an image source like an X-ray or the like. The added information may be referred to as overlay data. The overlay data may highlight or emphasize the contours of the device or may be any other information obtained from the frames of the raw image stream. For example, in cardiac applications, a stent position may be visually enhanced in relation to a vessel wall.

The overlay data are typically generated by an image processing algorithm. However, it takes a certain time to determine or generate the overlay data so that there may be a time lag between capturing the frames of the raw image stream and presenting the frames together with the assigned overlay data to a user.

SUMMARY OF THE INVENTION

There may thus be a need for reducing the time lag between capturing the raw image stream and presenting the frames of the raw image stream together with overlay data to an operator/user.

The object of the present invention is solved by the subject-matter of the independent claims; further embodiments are incorporated in the dependent claims. It should be noted that the following described aspects of the invention apply also for the image processing device, for the medical imaging arrangement for processing images, and for the method for processing images.

According to the present invention, an image processing device is provided. The image processing device comprises a processor, a data memory, an input interface, and an output interface. The input interface provides a raw image stream with a plurality of frames to the processor. The output interface provides an output image stream to a display.

The processor is configured to: receive the raw image stream; process the frames of the raw image stream by means of an image processing algorithm to thereby obtain a processed image stream, wherein the processed image stream is composed of the raw image stream and overlay data generated by the image processing algorithm containing additional information compared to the raw image stream; provide the processed frames of the raw image stream with the corresponding overlay data to the data memory; generate a selection of past frames of the raw image stream that already underwent processing by the image processing algorithm; to compare a current frame of the raw image stream with at least some frames of the selection of past frames and determine a similarity value for the current frame and the at least some frames of the selection of past frames; identify a matching frame of the selection of frames based on the similarity value to the current frame; assign the overlay data from said matching frame to the current frame, and add the current frame and the assigned overlay data from the matching frame to the output image stream.

This provides an output image stream that contains overlay data assigned to the data of the captured raw image stream. At least in a first stage, the overlay data of a current frame are the result of a similarity comparison between the current frame of the raw image stream and past frames of the raw image stream that already underwent image processing.

From those past frames of the raw image stream, a matching frame is selected that is relatively similar to the current frame. Then, the overlay data of that similar frame is selected and the selected overlay data is assigned to the current frame.

The matching frame, or similar frame, identified from the selection of the past frames is considered a close visual substitute for the current frame. Therefore, it can be assumed that the overlay data of the close visual substitute will also match the current frame. In an example, the matching frame is a most similar frame, in particular that frame from the selection of past frames for which the similarity value is highest. In other words, in this example, the matching frame is that past frame that is most similar to the current frame.

Thus, advantageously, instead of waiting for the processing results of a computationally expensive and time-consuming image processing algorithm that generates the overlay data for the current frame, the overlay data of the similar past frame is selected to be presented together with the current frame. The operation of comparing the current frame of the raw image stream to past frames of the raw image stream may require far less computing power than processing the current frame by means of the image processing algorithm. Therefore, the overlay data selected from the similar past frame is available for presentation to an operator/user sooner than the results of the image processing algorithm, preferably in (near) real time. Thereby, a time lag of presenting the frames of the raw image stream together with overlay data is eliminated or at least significantly reduced.

In other words, overlay data from a past frame that had already been processed is added together with the current image to the output image stream. The current frame is compared to a limited number of past frames using a similarity or matching algorithm that is computationally less expensive than the image processing algorithm. When a matching past frame has been identified, the overlay data for that matching past frame is added together with the current frame to the output image stream, for example for displaying to a medical practitioner. As a result, the time lag between the output image stream and the raw image stream is eliminated or at least significantly reduced.

This is beneficial for example in image guided medical procedures, where the image stream serves to provide real time feedback to a medical practitioner. In this situation, what a medical practitioner is doing is guided by live images on a display, for example fluoroscopy images from an interventional X-ray system. For this purpose, it is a requirement to display the live images in real time, without any processing delay.

According to an embodiment, the selection of frames has a predetermined size and contains a number of past frames corresponding to the predetermined size. In this embodiment, the processor may be configured to determine the selection of frames of the raw image stream by applying a sliding window algorithm to past frames of the raw image stream that passed an image processing algorithm. Alternatively, a selection is made based on a physiological parameter, such as a phase of the current frame within a cardiac or respiratory cycle.

Generally speaking, the selection of frames is composed of frames of the raw image stream that already underwent processing by an image processing algorithm to generate the relating overlay data. A selection of these processed frames is then generated as a basis for the comparison with the current frame. In an example, the sliding window algorithm may then select the most recent ones of the frames that were processed by the image processing algorithm. This approach may result in relatively high similarity between the frames of the selection of frames and the current frame.

In an example, the predetermined number of past frames should be small enough for the comparing of the current frame to each past frame in the selection to still be computationally feasible in real time.

According to an embodiment, the processor is configured to generate the overlay data based on the frames of the raw image stream and/or quantity values derived from the frames of the raw image stream.

According to an embodiment, the processor is configured to add an indication of the determined similarity value of the matching frame to the output image stream.

In this embodiment, an operator is provided with information about the degree of similarity between the current frame and the most similar past frame. This degree of similarity may indicate the degree of accuracy of the overlay data of the past frame presented together with the current frame.

According to an embodiment, the processor is configured to compare the similarity value of the matching frame to a similarity threshold value. Thus, for example, if the similarity value is smaller than the similarity threshold value, only the current frame is added to the output image stream, while both the current frame and overlay data of the matching past frame are added to the output image stream if the similarity value is equal to or larger than the similarity threshold value.

Accordingly, no overlay data are selected from the past frames to be presented to an operator/user together with the current frame if the similarity value is smaller than a predetermined similarity threshold value. The rationale behind this is to avoid presenting overlay data from past frames that are, to a certain extent, different from the current frame.

According to an embodiment, the processor is configured to compare the overlay data that were assigned to a first frame of the raw image stream based on the selection of frames with overlay data resulting from an image processing algorithm applied to the first frame.

In this embodiment, the overlay data that were assigned to a first frame based on the similarity comparison with the past frames is compared to the overlay data that are generated by an image processing algorithm based on that first frame. This approach enables comparing the level of correspondence between the initially assigned overlay data and the finally determined overlay data. The operator/user of the image processing device or of a medical imaging arrangement comprising such an image processing device may decide based on this information whether or not to use the overlay data estimation process (i.e., identifying overlay data based on the similarity between the current frame and a past frame) with reduced time lag or if the operator/user prefers to wait for the overlay data actually resulting from a time-consuming image processing algorithm.

According to the present invention, also a medical imaging arrangement for processing images is provided. The medical imaging arrangement comprises an image sensor, a display, and an image processing device as described in one or more embodiments above and hereinafter. The image sensor is communicatively coupled to the image processing device to provide a raw image stream to the image processing device and the display is communicatively coupled to the image processing device to receive an output image stream from the image processing device.

According to an embodiment, the imaging system is an X-ray system, in particular an interventional X-ray system that may provide live X-ray images during an image guided medical intervention. Alternatively, the imaging system may be an echocardiography device, an ultrasound device, a photoacoustic imaging device, or the like.

The image sensor may be any device suitable for capturing images in accordance to the technology of a particular imaging system. The image sensor may be a device that is specifically designed for a certain imaging system technology. However, the image sensor may provide the raw image stream in accordance with known standards so that an interface between the image sensor and the image processing device is standardized and does not need to be adapted to different imaging technologies. Nonetheless, the image processing device may contain proprietary interfaces to be communicatively coupled to different image sensors.

The display may be any type of device suitable for visually displaying information to a human operator/user. For example, the display may be a monitor or a plurality of monitors, a touch screen or a head-mounted display.

Of course, the principles as presented with respect to the image processing device apply to the medical imaging arrangement.

According to the present invention, also a method for processing images is provided. The method comprises the following steps: receiving a raw image stream with multiple frames; processing the frames of the raw image stream using an image processing algorithm to thereby obtain a processed image stream, wherein the processed image stream is composed of the raw image stream and overlay data generated by the image processing algorithm containing additional information compared to the raw image stream; providing the processed frames of the raw image stream with the corresponding overlay data to a data memory; generating a selection of past frames of the raw image stream that already underwent processing by the image processing algorithm; comparing a current frame of the raw image stream with at least some frames of the selection of past frames; determining a similarity value for the current frame and at least some frames of the selection of past frames; identifying a matching frame of the selection of frames based on the similarity value to the current frame; assigning the overlay data from the identified frame of the selection of frames to the current frame; and adding the current frame and the assigned overlay data from the matching frame to the output image stream.

Functional features described above with reference to embodiments of the image processing device may be implemented as method steps of the method for processing images.

Furthermore, a computer program element is provided. The computer program element is configured for controlling an image processing device as described herein, which, when being executed by a processing unit, is adapted to perform the method steps of a method for processing images described herein.

Last, a computer readable medium is provided having stored the computer program element thereon.

According to an aspect, the devices and methods described herein relate to latency compensation for image processing devices in particular for use in system for use in image guided medical procedures. In order to assign overlay data to frames of a raw image stream, past frames within a selection of frames of the raw image stream are considered, which past frames already underwent image processing by an image processing algorithm. A current frame of the raw image stream is compared to the past frames contained in the sliding window, and that one of the past frames is identified that is most similar to the current frame. Overlay data from the identified past frame are chosen and assigned to the current frame. Thus, the current frame can be presented together with the assigned overlay data chosen from the most similar past frame and without the need to wait for the result of a computationally expensive and time-consuming image processing of the current frame.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

Figure 1:
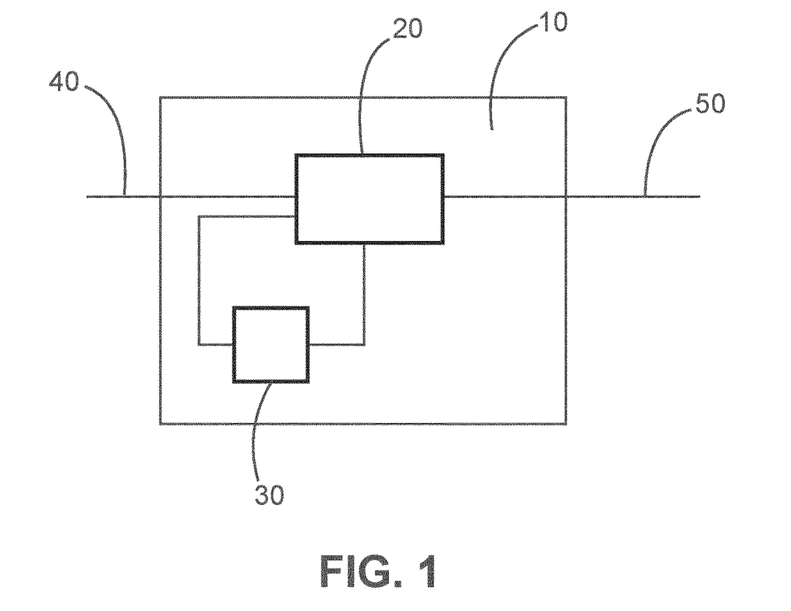
FIG. 1 schematically shows an image processing device according to an embodiment.

FIG. 1 schematically shows an embodiment of an image processing device 10.

The device 10 comprises a processor 20, a data memory 30, an input interface 40, and an output interface 50. The input interface 40 is configured to provide a raw image stream with a plurality of frames to the processor 20. The output interface 50 is configured to provide an output image stream to a display.

The processor 20 is configured to receive the raw image stream, process the frames of the raw image stream to thereby obtain a processed image stream, wherein the processed image stream is composed of the raw image stream and overlay data containing additional information compared to the raw image stream, whereby the overlay data is generated by the image processing algorithm.

The raw image stream and the generated overlay data are provided to the data memory 30. The processor 20 is further configured to then generate a selection of frames of past frames of the raw image stream, compare a current frame of the raw image stream with at least some frames of the selection of past frames, determine a similarity value for the current frame and at least some frames of the selection of frames, and identify a matching frame based on the similarity value.

Finally, the processor 20 is configured to assign the overlay data from the matching past frame, which had already been processed using the image processing algorithm, and to add the current frame and the assigned overlay data to the output image stream.

A benefit of this approach is to compensate for latency that is introduced by computational demanding and/or time-consuming image processing algorithms applied to frames of an image stream.

For example, if additional information, i.e., the overlay data, are to be generated from the frames and rendered into an image stream, this process requires a certain amount of time. Depending on the image processing algorithms, the time lag introduced by the image processing stream may be significant. For some applications, in particular applications in medical image-guided interventions, a time lag of several tens of milliseconds may already be undesirable or inacceptable, as it causes what the practitioner is seeing on the display to lag behind what he is actually doing thereby hindering the performance of the intervention or procedure.

The compensation of the latency is done by comparing current image frames of a real-time image stream, i.e., the raw image stream, with past frames of the same real-time image stream that already underwent the image processing algorithm to determine the overlay data. The overlay data may be results of the image processing algorithm, wherein the results are rendered into the individual frames of the real-time image stream.

For diagnostic imaging processes, additional information is rendered into the raw image stream, for example overlay image data enhancing a catheter tip or stent, to make visual inspection of the displayed image frames easier and more comfortable. In this example, when the catheter tip is moved, latency between the tip movement and the processed image stream is introduced because rendering the information relating to the catheter tip into the raw image stream is a process that is computationally costly. As a result of this latency, a displayed image of a catheter tip or stent together with the enhancing overlay no longer accurately represents the live situation.

The raw image stream comprises multiple frames. The most recent frame is referred to as current frame. However, in order to render the additional information into the current frame, a certain amount of processing time is required which introduces time lag.

The raw image stream originates from an image source, e.g., a fluoroscopy imaging device like an X-ray device, ultrasonic device and the like.

At least some or all past frames of the raw image stream and the assigned overlay data are at least temporarily stored in the data memory 30. A selection of frames of the raw image stream are considered for being compared with the current frame of the raw image stream. Comparing two images, i.e., comparing the current frame of the raw image stream with at least one, more, or each of the selection of past frames of the raw image stream, requires far less computation time than image processing operations. The current frame of the raw image stream is compared to at least one, some, or each of the frames of the selection of past frames of the raw image stream. Thus, multiple image comparison operations are carried out, wherein a respective image comparison operation is applied to two images, i.e., the current frame and one past frame. For at least some of these image comparison operations, a similarity value is calculated for the pair of compared frames. Then, the pair of frames with the highest similarity is selected to identify a past frame that is most similar to the current frame. Based on the identified most similar past frame, the overlay data rendered into that (past) frame is selected from the data memory and also rendered into the current frame of the raw image stream. The additional information that is rendered into the frames of the raw image stream is referred to as overlay data. The frames of the raw image stream and the overlay data are presented to an operator of an imaging device.

For example, in cardiac applications, this approach helps to visually enhance the catheter tip in relation to a vessel wall with a small time lag. The visually enhanced optical characteristics are overlaid to the frames of the raw image stream to highlight or emphasize features of the frames of the raw image stream. This composition of optical features, i.e., frames of the raw image stream and the additional optical characteristics, are referred to as processed image stream.

Comparing the current frame of the raw image stream with the past frames of the raw image stream can be done by any applicable image comparing and/or image similarity determining algorithm. For example, at least some of structures, lines, shapes, brightness appearing in those frames can be taken into consideration in order to calculate a similarity value. For example, the similarity value can be calculated by sum of squared differences between intensity values of the frames. It is assumed that the image processing results of similar frames are similar. This is why the additional information rendered into a past frame can be rendered into the current frame if the current frame is identical or similar (to a certain degree) to said past frame.

In one embodiment, the comparison may be done by using only a selected part or selected region of the past frames. For example, the selected region around the overlay data is considered for comparison with the current frame. The selected region around the overlay data may be defined as that region of a past frame where the overlay data is located. The selected region is larger than the overlay data. Furthermore, in the comparison process, an image transformation like a shift between a region of interest of the past images with respect to the current frame may be determined. When assigning the overlay data of a past frame to the current frame, the transformation may also be applied to the overlay data.

In other words, in an example, a current frame is compared to a selection of past frames that already underwent image processing and is assigned to overlay data, identifying a similar past frame, for example that one of the past frames that is most similar to the current frame, and compose an output image stream based on the current frame and the overlay data of the selected past frame.

Figure 2:
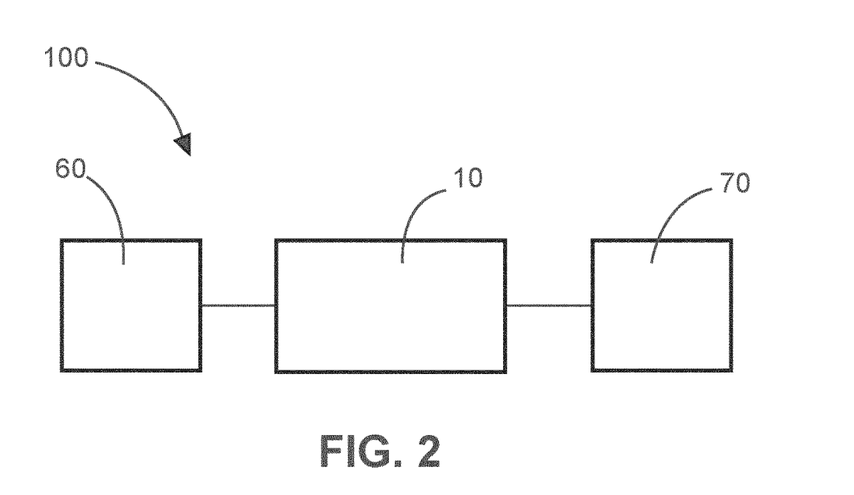
FIG. 2 schematically shows an imaging arrangement according to an embodiment.

FIG. 2 exemplarily shows a medical imaging arrangement 100. The imaging arrangement 100 comprises an image sensor 60, an image processing device 10, for example the device described with reference to FIG. 1, and a display 70. The image sensor 60 is communicatively coupled to the image processing device to provide a raw image stream to the image processing device. Particularly, the image sensor 60 provides the raw image stream to an input interface 40 of the image processing device 10 and the input interface provides the raw image stream to the processor 20. For example, the image sensor 60 may be coupled to the image processing device 10 by a wired or wireless connection. In one embodiment, the image sensor 60 and the image processing device 10 may be connected by a data transmission network that is comprises of multiple segments of which some may be wired segments and others may be wireless segments. The display 70 is communicatively coupled to the image processing device 10 to receive an output image stream from the image processing device. For the communicative coupling of the display 70 and the device 10, the same principles apply as described with reference to the coupling of the image sensor 60 and the image processing device 10.

It is noted that the imaging system 100 of FIG. 2 may comprise the image processing device 10 described with reference to any embodiment or example contained herein.

According to an embodiment, the imaging system 100 is an X-ray system, an echocardiography device, an ultrasound device, a photoacoustic imaging device, or the like.

The image sensor 60 may be any device suitable for capturing images in accordance to the technology of a particular imaging system. The image sensor 60 may be a device that is specifically designed for a certain imaging system technology. However, the image sensor 60 may provide the raw image stream in accordance with known standards so that an interface between the image sensor 60 and the image processing device 10 is standardized and does not need to be adapted to different imaging technologies. Nonetheless, the image processing device may contain proprietary interfaces to be communicatively coupled to different image sensors.

The principles of image processing as implemented by the image processing device 10 and the method for image processing disclosed herein are further described with reference to FIG. 3 to FIG. 6.

Figure 3:
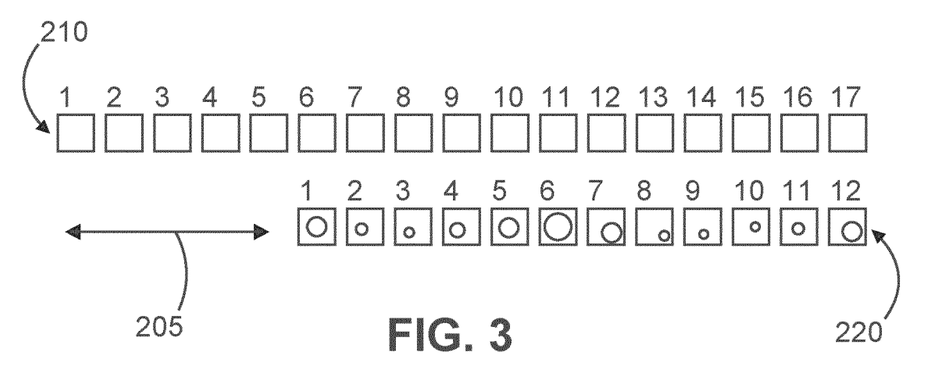
FIG. 3 schematically shows a raw image stream and a time lag resulting from an image processing algorithm applied to the frames of the raw image stream.

FIG. 3 shows a raw image stream 210 with multiple frames numbered from 1 to 17 in accordance with the time these frames are captured and/or provided to the image processing device. In other words, frame 1 is provided first, then, after a certain amount of time, frame 2 is provided, etc.

When applying an image processing algorithm to the individual frames in order to generate overlay data for the frames, this operation requires a certain amount of time depending on the complexity of the image processing algorithm. The time required for finishing image processing for a frame is indicated by the time lag 205. The processed images are the output of an image processing algorithm and overlay data are assigned to at least some or all frames of the raw image stream. The overlay data are shown by circles within the individual frames. However, it is noted that the overlay data may be any data generated based on the frames of the raw image stream. Examples of overlay data are provided above and hereinafter with reference to other examples and embodiments.

Figure 4:
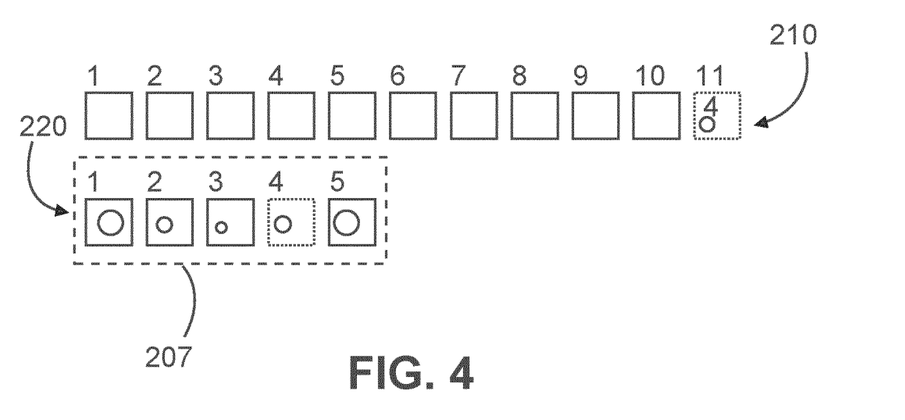
FIG. 4 schematically shows assigning overlay data of past frames to a current frame of a raw image stream.

FIG. 4 shows a raw image stream with eleven frames and frame 11 being the most recent frame, i.e., the current frame. In this embodiment, it is assumed that frames 1 to 5 of the raw image stream 210 underwent image processing by the image processing algorithm and the overlay data for frames 1 to 5 are available, such that the frames 1 to 5 with the assigned overlay data correspond to the processed images 220.

In one embodiment and with reference to the image processing device 10 of FIG. 1, the processor 20 is configured to determine the selection of frames of the raw image stream by applying a sliding window algorithm to past frames of the raw image stream that passed an image processing algorithm.

The selection of frames corresponds to the sliding window 207, which in this example contains five frames (frame 1 to frame 5) of the processed images 220. The current frame, i.e., frame 11, of the raw image stream 210 is compared to at least one, some or all frames that are contained in the sliding window 207 to determine the most similar frame within the sliding window. For example, if it is determined that frame 4 of the sliding window 7 is most similar to the current frame 11, the overlay data of frame 4 are selected and assigned to and rendered into the current frame. In FIG. 4, frame 11 (current frame) and frame 4 (the past frame that is most similar to the current frame) are shown with dotted lines for purposes of illustration only and in order to point out that these two frames are most similar to each other.

At least some or each of the frames of the selection of frames of the raw image stream is compared to the current frame of the raw image stream. The likelihood for finding a similar frame may increase when comparing frames that are captured about the same time or in temporal proximity. Therefore, once a frame is processed, it is entered into the selection of frames as the most recent frame that passed image processing. The entirety of frames of the current image stream that have passed image processing may be referred to as processed image stream. Thus, the frames of the processed image stream are those frames for which the image processing algorithm has finished identifying the overlay data.

In an example, the most recent frame of the processed image stream steps into the selection and the most past frame of the processed image stream drops out of the selection. In other words, thus, the selection comprises a sliding window of processed frames that works like a buffer that implements the first-in-first-out principle.

In one embodiment, other parameters that are known to affect the image similarity may be used to select the past frames contained within the sliding window. For example, in a periodical process, frames taken during the same or close to the same point of time with reference to the periodic process. Specifically, if the current frame is taken from the human heart and during an end-diastolic heart phase, the sliding window may contain past frames that were taken close to or during end-diastolic heart phase from previous heartbeat cycles. Similarly, if a current frame is acquired at another time in the cardiac cycles, a selection of past frames acquire at or around the same time could be envisaged.

Figure 5:
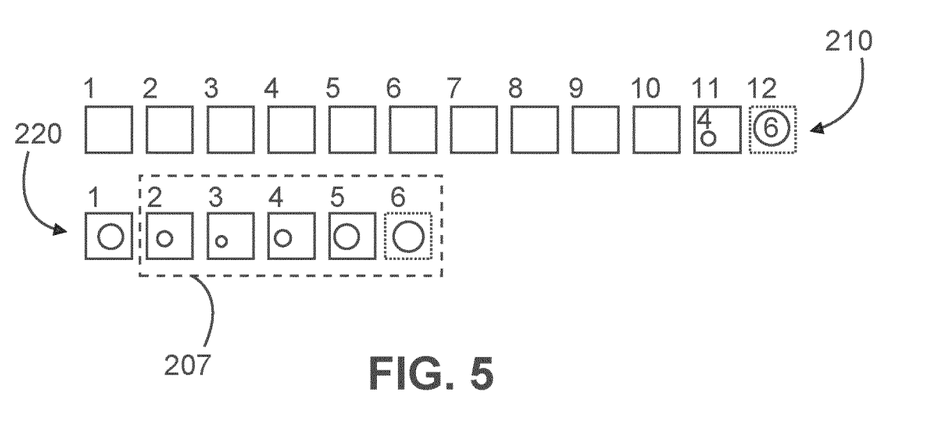
FIG. 5 schematically shows assigning overlay data of past frames to a current frame of a raw image stream.

FIG. 5 exemplarily shows the scenario that follows the scenario shown in FIG. 4. In the example shown in FIG. 5, the raw image stream 210 contains twelve frames with frame 12 being the current frame. At this point in time, one more frame might have undergone image processing by the image processing algorithm so that the processed images 220 contain six frames, i.e., frame 1 to frame 6. The sliding window 207 shifts one position to the right to contain the most recent five frames, i.e., frame 2 to frame 6. The current frame 12 is compared to frames 2 to 6 within the sliding window to identify the most similar frame (in this embodiment: frame 6) and to then select the overlay data from that most similar past frame and render the selected overlay data into frame 12. As can be seen in FIG. 5, the sliding window contains the most recent frames of the processed images. In FIG. 5, frame 12 (current frame) and frame 6 (the past frame that is most similar to the current frame) are shown with dotted lines for purposes of illustration only and in order to point out that these two frames are most similar to each other.

In the embodiment described with reference to FIG. 4 and FIG. 5, the size of the sliding window 207 is five frames. However, it is noted that the size of the sliding window may be different from this size and may also vary during operation of the image processing device.

In one embodiment and with reference to the image processing device 10 of FIG. 1, the processor 20 is configured to adjust a number of frames within the selection of frames. Hence, the size of the sliding window is adjusted, i.e., increased or decreased.

In one embodiment and with reference to the image processing device 10 of FIG. 1, the processor 20 is configured to generate the overlay data based on the frames of the raw image stream and/or quantity values derived from the frames of the raw image stream.

The overlay data may either highlight elements contained in the frames of the raw image data or add a derived quantity to overlay the frames, e.g., cardiac volume or cardiac dimensions and to be displayed together with the frames. For example, the complete body of a structure may be labelled, or an algorithm may process a frame of the raw image stream and output a quantity value without labelling individual landmarks in the frame that lead to said quantity value. Furthermore, in one embodiment, the overlay data may be generated based on contours contained in the frames of the raw image stream.

In one embodiment and with reference to the image processing device 10 of FIG. 1, the processor 20 is configured to process multiple frames of the raw image stream 210 in parallel to thereby obtain a respective frame of the processed image stream 220 from each processing operation that is executed in parallel.

Assuming that the processing time per frame of the raw image stream takes about a constant time, the processor must be able to process multiple frames in parallel when the processing time is larger than the time between two subsequent frames of the raw image stream in order not to extend the processing time per individual frame. For example, with a frame rate of 20 to 25 frames per second and a processing time of the algorithm that calculates the frames of the processed image stream of two seconds per frame, the processor must be able to process 50 frames in parallel in order not to extend the processing time per individual frame.

The processor may process at least some or each frame of the raw image stream in accordance with the principles set forth herein. However, in case of reduced computational power, the processor may process every second frame (or every third or higher number of frames) of the raw image stream.

In one embodiment and with reference to the image processing device 10 of FIG. 1, the processor 20 is configured to add the determined similarity value of the identified frame of the selection of frames with the highest similarity value to the output image stream.

The selection of past processed frames may not contain a frame that is absolutely identical to the current frame. For this reason, it might be helpful for an operator of an imaging device to know a grade of similarity between the current frame and the identified most similar frame of the selection of past frames. This grade of similarity may be an indication of how accurate the overlay data of the past frame fit to the current frame. The similarity value or a percentage value indicating the similarity between the current frame and the selected past frame may be displayed on the display 70 together with the frames of the output image stream.

In one embodiment and with reference to the image processing device 10 of FIG. 1, the processor 20 is configured to compare the similarity value of the identified frame with the highest similarity value to a similarity threshold value, and generate the output image stream to indicate if the similarity value is smaller than the similarity threshold value or equal to or larger than the similarity threshold value.

This allows for defining a similarity threshold value which indicates the minimum required similarity in order to generate minimum reliable output image streams based on the past frames. In this embodiment, the device indicates if the similarity between the current frame and the most similar past frame (of the selection of frames) is above or below the similarity threshold value. In case the similarity value is below the similarity threshold value, the output result may not be reliable to proceed with and the operator may choose to wait on the results of the image processing algorithm.

For example, either similarity value and/or a symbol may be displayed to indicate if the similarity values is smaller or greater than the similarity threshold.

In one embodiment and with reference to the image processing device 10 of FIG. 1, the processor 20 is configured to stop adding the overlay data to the current frame if the similarity value is smaller than the similarity threshold value.

In this embodiment, the overlay data is not added to the current frame when the similarity is too low so that an operator of the image device is not misled by possible inaccurate overlay data.

In one embodiment and with reference to the image processing device 10 of FIG. 1, the processor 20 is configured to compare the overlay data that were assigned to a first frame of the raw image stream based on the selection of frames with overlay data resulting from an image processing algorithm applied to the first frame.

Figure 6:
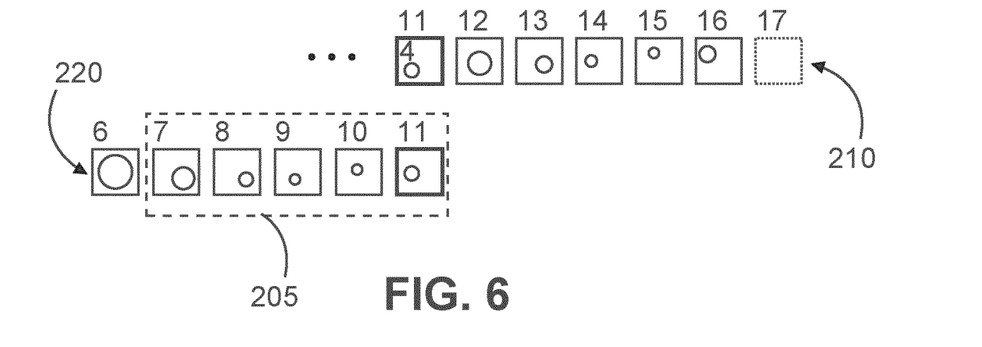
FIG. 6 schematically shows comparing the assigned overlay data of a frame to generated overlay data of that frame.

FIG. 6 is based on the embodiment shown in FIG. 4 and describes this embodiment in more details. As described with reference to FIG. 4, frame 11 of the raw image stream 210 is initially assigned the overlay data of frame 4 that was the most similar frame from the sliding window 207 at the time when frame 11 was captured or provided by the image sensor. However, FIG. 6 shows the scenario at a later time when frame 11 of the raw image stream 210 was processed by the (time-consuming) image processing algorithm. At the time shown in FIG. 6, the actual processing result of frame 11 is available and at this time, the overlay data initially assigned to frame 11 (see FIG. 4) can be compared to the overlay data resulting from the image processing algorithm (see FIG. 6). This comparison allows for determining the accuracy of the initially assigned overlay data. In FIG. 6, frame 17 is shown with dotted lines for purposes of illustration only and in order to point out that this frame is the current frame.

In other words, this embodiment allows for comparing the current image frame of the raw image stream together with the overlay data derived from the selection of past frames (may be referred to as estimated output) with the result of said current image frame being processed by an image processing algorithm (may be referred to as processed output). The accuracy of the estimated output depends on the grade of similarity between the current frame and the frames of the selection of past frames. If the past frames have a low level of similarity to the current frame, then the overlay data selected from the past frames and assigned to the current frame may also have a low accuracy. On the other hand, the processing results of the image processing algorithm are highly accurate. Therefore, this embodiment allows for determining the accuracy of the initially assigned overlay data in view of the overlay data resulting from the image processing algorithm.

In more details, a first frame of the raw image stream is assigned overlay data from a past frame that meets similarity criteria. This initially assigned overlay data may be referred to as estimated overlay data. However, this first frame undergoes image processing and at some time in the future, the processing results of the image processing are available. The processing results contain the computed overlay data based on the first frame. Then, the computed overlay data (result of the image processing algorithm) and the estimated overlay data (selected from the most similar past frame) are compared to each other to determine a similarity between these different overlay data.

With further reference to FIG. 3 to FIG. 6, an approach is described for compensating for visual latency introduced by image analysis algorithms when their results are rendered into real-time fluoroscopy.

In this approach, a general method and device is described which allows to use computational costly image processing algorithms or algorithms hosted in a cloud computation center without introducing significant additional latency into the feedback loop. The display of frames and processing results remain synchronized and real-time although the transmission of images to the cloud may introduce significant latency.

Therefore, an additional, fast algorithm (the algorithm that compares the current frame to the already processed past frames) calculates for at least some or each frame in a sliding window 207 of frames (back in time) the image similarity to the current frame. The sliding window is positioned in such a way that for all frames in the sliding window 207 the processing result is available. In an example, the most similar frame within the sliding window can be seen as the best available visual substitute for the current frame, hence it is assumed herein that the corresponding processing result is also close to the processing of the current frame (although the actual processing result of the current frame is not available yet). For the current frame the substitute processing result is overlaid to the original stream (raw image stream) and the original frame together with the overlay data from the selected past frame are added to the output image stream.

When the current frame has been processed (a short time later) the processor compares the initially assigned overlay data (back in time) with current, true result. If this comparison reveals a significant error, this may be indicated at the display to the operator and/or the assigning of overlay data from past frames to the respective current frame may be completely disabled As an application example, during interventional X-ray, the operator may interactively change the position of a catheter tip/stent while visually inspecting the displayed image frames. In many interventional guidance applications not only the image frames are shown but also additional information (the overlay data), which is simultaneously extracted from the images. For example, in cardiac applications the stent position can be visually enhanced in relation to the vessel wall working against. A dedicated processing algorithm may fade out background noise and unwanted anatomical structures in the real-time image stream.

The additional processing by the image processing algorithm to calculate the overlay data usually introduces some latency between the tip movement and the output image stream. Only latency on the order of several hundreds of milliseconds may be accepted, otherwise catheter tip movements and image information may no longer be synchronized and make it difficult for the operator to relate the effect of the tip movement to the change of the visual image content.

The approach described herein allows to use computational costly image processing algorithms and/or transmission channels (for example connection between the image sensor 60 and the image processing device 10 on the one hand and connection between the image processing device 10 and the display 70 on the other hand) without introducing significant latency into the feedback loop. The display of frames and processing results remain synchronized and real-time, although the overall data transmission and processing is on the order of several seconds per frame.

In FIG. 4, the segmentation result (result of the image processing algorithm) of frame 11 is unknown and the segmentation result of frame 4 is used and assigned to frame 11. However, after the acquisition of frame 17 (see FIG. 6) the true segmentation result of frame 11 is known. As depicted in FIG. 6 the substitute overlay data of frame 4 and the true segmentation result of frame 11 can now be compared to each other and quantitatively characterized to identify and indicate the accuracy of the initially assigned overlay data from frame 4 to frame 11. This indicates how close the overlay data of frame 4 were to the actually computed overlay data of frame 11. This step can be executed for the following frames as well and a sliding average may be presented to an operator/user as a retrospective quality measure or error measure in the display together with the current frames and overlay data. Based on the presented information, the operator may qualify how good the similarity algorithm has worked just a few frames before, and if the measure is below a certain quality threshold, the overlay data taken from the past frames will no longer be shown, as described with reference to certain embodiments. If the quality improves, the overlay data may be displayed again.

In one embodiment, a ventricle within the human body may be used for the segmentation of the ventricle as a guiding anatomical structure. However, a ventricle is used only for illustration. Any processing task which is based on individual frames (2D or 3D) can be used. With a frame rate of 20-25 frames per second and a processing time of 2 seconds per frame the algorithm may allow to process 50 frames in parallel without extending the processing time per individual frame.

The length of the sliding window can be larger as described above with reference to one embodiment, it can also vary over time, e.g., be increased or decreased over time. The calculation of the similarity measure may be on the order of several microseconds to meet the real-time constraints of ultrasound. Also, other similarity metrics can be used.

For cardiac applications, the similarity can be assessed not only frame by frame but also on the basis of complete heart cycles, hence the entire sequence of frames is compared (in one step) or the frame by frame comparison is guided position of the frames within the cycle to reduce the overall size of the sliding window.

The approach described herein may also be used in Ultrasound applications. In this case, the operator may not move a catheter tip or stent but a probe which steers the image formation process.

Figure 7:
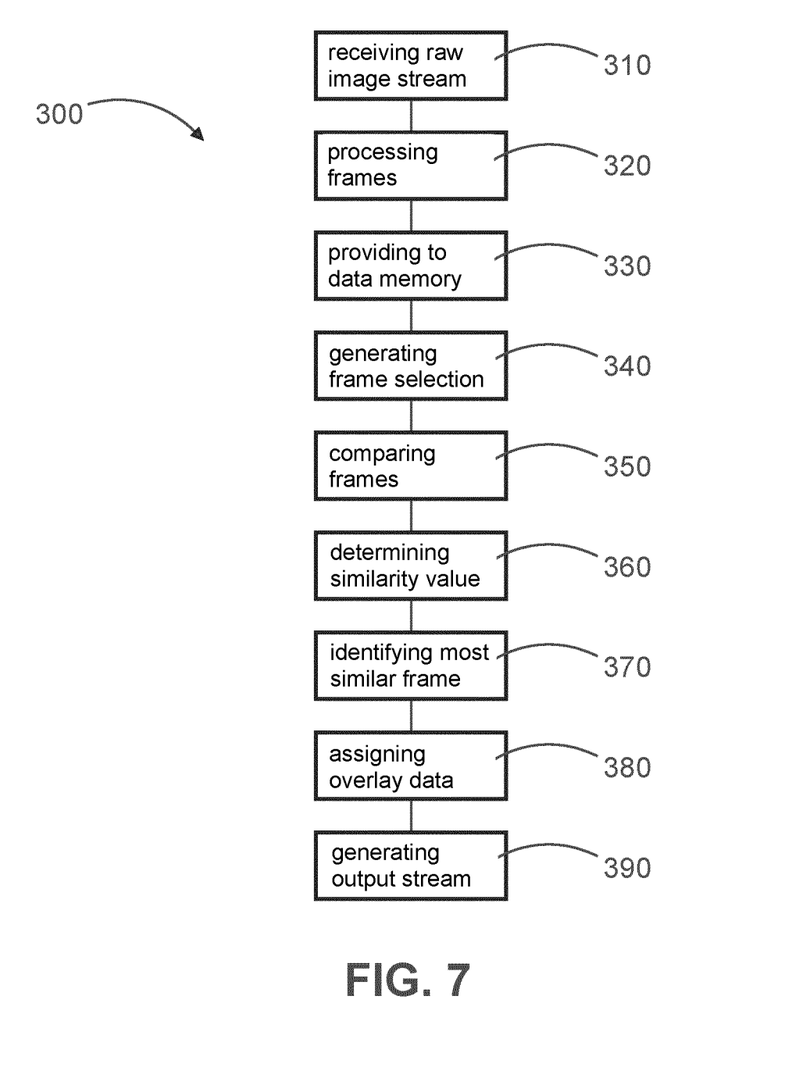
FIG. 7 schematically shows the steps of a method for processing images according to an embodiment.

FIG. 7 shows an embodiment of a method 300 for processing images. In this embodiment, the method 300 comprises the following steps:

step 310: receiving a raw image stream with multiple frames step 320: processing the frames of the raw image stream using an image processing algorithm to thereby obtain a processed image stream, wherein the processed image stream is composed of the raw image stream and overlay data generated by the image processing algorithm, which contains additional information compared to the raw image stream;

step 330: providing the processed frames of the raw image stream and the overlay data to a data memory;

step 340: generating a selection of past frames of the raw image stream, which past frame already underwent processing by the image processing algorithm;

step 350: comparing a current frame of the raw image stream with at least some frames of the selection of frames;

step 360: determining a similarity value for the current frame and at least some frames of the selection of past frames;

step 370: identifying a matching frame of the selection of past frames based on its similarity to the current frame;

step 380: assigning the overlay data from the identified frame of the selection of frames to the current frame;

step 390: adding the current frame and the assigned overlay data from the matching past frame to the output image stream.

For the method 300 schematically shown in FIG. 7, the same principles apply as described with reference to the image processing device 10 and the medical imaging arrangement 100 described with reference to FIG. 1 to FIG. 6. Functional features described with reference to the image processing device 10 and the medical imaging arrangement 100 may be implemented as additional or optional steps of the method 300.

In one embodiment, the method comprises the steps of comparing the similarity value of the identified frame with the highest similarity value to a similarity threshold value, and generating the output image stream to indicate if the similarity value is smaller than the similarity threshold value or equal to or larger than the similarity threshold value.

In another embodiment, the method comprises the step of comparing the overlay data that were assigned to a first frame of the raw image stream based on the selection of frames with overlay data resulting from an image processing algorithm applied to the first frame.

In another exemplary embodiment of the present invention, a computer program or a computer program element is provided that is characterized by being adapted to execute the method steps of the method according to one of the preceding embodiments, on an appropriate system, e.g., when being executed by a processing unit like the processor 20.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor like the processor 20. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit or processor 20, for instance a controller, implements the method as described with reference to some embodiments. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A image processing device, comprising:
a processor configured to:
obtain a raw image stream with a plurality of frames;
process the plurality of frames of the raw image stream to generate a processed image stream comprising a subset of the plurality of frames of the raw image stream and overlay data containing additional information compared to the raw image stream, wherein the processor is configured to generate the overlay data by image processing of the subset of the plurality of frames of the raw image stream;
select past frames from the processed subset of the plurality of frames;
compare a raw image frame of the raw image stream with each past frame of the selection of past frames to determine a similarity value for the raw image frame and each past frame;

identify a matching frame of the selection of past frames based on the similarity value;

assign the overlay data from the matching frame to the raw image frame; and add the raw image frame and the assigned overlay data from the matching frame to an output image stream.

2. The image processing device according to claim 1, wherein:

the selection of past frames has a predetermined size and contains a number of past frames corresponding to the predetermined size, and the processor is further configured to:

determine the selection of past frames by applying a sliding window to past frames of the raw image stream.

3. The image processing device according to claim 2, wherein the processor is further configured to:

adjust a number of past frames within the selection of past frames.

4. The image processing device according to claim 1, wherein the processor is further configured to:

generate the overlay data based on at least one of the frames of the raw image stream or quantity values derived from the frames of the raw image stream.

5. The image processing device according to claim 1, wherein the processor is further configured to:

process multiple frames of the raw image stream in parallel to obtain a respective processed frame of the processed image stream from each processing operation that is executed to process the multiple frames in parallel.

6. The image processing device according to claim 1, wherein the processor is further configured to:

add an indication of the determined similarity value of the matching frame to the output image stream.

7. The image processing device according to claim 1, wherein the processor is further configured to compare the similarity value of the matching frame to a similarity threshold value.

8. The image processing device according to claim 7, wherein the processor is further configured to:

stop adding the overlay data to the raw image frame if the similarity value of the matching frame is smaller than the similarity threshold value.

9. The image processing device according to claim 1, wherein the processor is further configured to:

compare the overlay data assigned to a first frame of the raw image stream based on the selection of past frames with overlay data resulting from an image processing algorithm applied to the first frame.

10. A medical imaging system for processing images, the system comprising:

the image processing device according to claim 1;

an image sensor communicatively coupled to the image processing device to provide the raw image stream to the image processing device; and a display communicatively coupled to the image processing device to receive the output image stream from the image processing device.

11. A method for processing images, the method comprising:

obtaining a raw image stream with a plurality of frames;

processing the plurality of frames of the raw image stream to generate a processed image stream comprising a subset of the plurality of frames of the raw image stream and overlay data containing additional information compared to the raw image stream, wherein the overlay data is generated by image processing of the subset of the plurality of frames of the raw image stream;

selecting past frames of the raw image stream from the processed subset of the plurality of frames;

comparing a raw image frame of the raw image stream with each past frame of the selection of past frames to determine a similarity value for the raw frame and each past frame;

identifying a matching frame of the selection of past frames based on the similarity value;

assigning the overlay data from the matching frame to the raw image frame; and adding the raw image frame and the assigned overlay data to an output image stream.

12. The method according to claim 11, further comprising:

comparing the similarity value of the matching frame to a similarity threshold value, and at least one of:

adding the raw image frame and the assigned overlay data to the output image stream if the similarity value of the matching frame is equal to or larger than the similarity threshold value, or adding the raw image frame to the output image stream only if the similarity value of the matching frame is smaller than the similarity threshold value.

13. The method according to claim 11, further comprising:

comparing the overlay data assigned to a first frame of the raw image stream based on the selection of past frames with overlay data resulting from an image processing algorithm applied to the first frame.

14. A non-transitory computer-readable storage medium having stored a computer program comprising instructions, which, when executed by a processor, cause the processor to:

obtain a raw image stream with a plurality of frames;

process the plurality of frames of the raw image stream to generate a processed image stream comprising a subset of the plurality of frames of the raw image stream and overlay data containing additional information compared to the raw image stream, wherein the processor is configured to generate the overlay data by image processing of the subset of the plurality of frames of the raw image stream;

select past frames from the processed subset of the plurality of frames;

compare a raw image frame of the raw image stream with each past frame of the selection of past frames to determine a similarity value for the raw image frame and each past frame;

identify a matching frame of the selection of past frames based on the similarity value;

assign the overlay data from the matching frame to the raw image frame; and add the raw image frame and the assigned overlay data from the matching frame to an output image stream.

15. The non-transitory computer-readable storage medium according to claim 14, wherein the instructions, when executed by the processor, further cause the processor to:

process multiple frames of the raw image stream in parallel to obtain a respective processed frame of the processed image stream from each processing operation that is executed to process the multiple frames in parallel.

16. The non-transitory computer-readable storage medium according to claim 14, wherein the instructions, when executed by the processor, further cause the processor to:
compare the similarity value of the matching frame to a similarity threshold value, and
at least one of:
add the raw image frame and the assigned overlay data to the output image stream if the similarity value of the matching frame is equal to or larger than the similarity threshold value, or
add the raw image frame to the output image stream only if the similarity value of the matching frame is smaller than the similarity threshold value.

17. The non-transitory computer-readable storage medium according to claim 14, wherein the instructions, when executed by the processor, further cause the processor to:
compare the overlay data assigned to a first frame of the raw image stream based on the selection of past frames with overlay data resulting from an image processing algorithm applied to the first frame.

18. The non-transitory computer-readable storage medium according to claim 14, wherein:
the selection of past frames has a predetermined size and contains a number of past frames corresponding to the predetermined size, and
the instructions, when executed by the processor, further cause the processor to:
determine the selection of past frames by applying a sliding window to past frames of the raw image stream.

19. The non-transitory computer-readable storage medium according to claim 14, wherein the instructions, when executed by the processor, further cause the processor to:
adjust a number of past frames within the selection of past frames.

20. The non-transitory computer-readable storage medium according to claim 14, wherein the instructions, when executed by the processor, further cause the processor to:
generate the overlay data based on at least one of the frames of the raw image stream or quantity values derived from the frames of the raw image stream.

* * * * *